United States Patent
Li et al.

(10) Patent No.: US 10,278,252 B2
(45) Date of Patent: *Apr. 30, 2019

(54) SOLID-STATE CIRCADIAN RHYTHM LAMP AND LUMINAIRE AND RELATED CONTROL TECHNIQUES

(71) Applicants: Ming Li, Acton, MA (US); Arunava Dutta, Winchester, MA (US); Anne Janet Milliez, Cambridge, MA (US); Ravidasa Hegde, Andover, MA (US); Vidisha Gupta, San Jose, CA (US); Philip Gerard Rioux, Brentwood, NH (US)

(72) Inventors: Ming Li, Acton, MA (US); Arunava Dutta, Winchester, MA (US); Anne Janet Milliez, Cambridge, MA (US); Ravidasa Hegde, Andover, MA (US); Vidisha Gupta, San Jose, CA (US); Philip Gerard Rioux, Brentwood, NH (US)

( * ) Notice: Subject to any disclaimer, the term of this patent is extended or adjusted under 35 U.S.C. 154(b) by 24 days.

This patent is subject to a terminal disclaimer.

(21) Appl. No.: 16/009,763

(22) Filed: Jun. 15, 2018

(65) Prior Publication Data

US 2018/0295696 A1 Oct. 11, 2018

Related U.S. Application Data

(63) Continuation-in-part of application No. 15/479,882, filed on Apr. 5, 2017, now Pat. No. 10,004,122.

(Continued)

(51) Int. Cl.
*H05B 33/08* (2006.01)
*A61N 5/06* (2006.01)

(Continued)

(52) U.S. Cl.
CPC ........ *H05B 33/0863* (2013.01); *A61M 21/02* (2013.01); *A61N 5/0618* (2013.01); *H05B 33/0845* (2013.01); *A61M 2021/0044* (2013.01); *A61M 2021/0083* (2013.01); *A61M 2205/3569* (2013.01); *A61M 2205/3584* (2013.01); *A61M 2205/3592* (2013.01); *A61M 2205/50* (2013.01);

(Continued)

(58) Field of Classification Search
None
See application file for complete search history.

(56) References Cited

U.S. PATENT DOCUMENTS

2010/0244740 A1* 9/2010 Alpert ................ H05B 37/0281
315/297

* cited by examiner

*Primary Examiner* — Dedei K Hammond
(74) *Attorney, Agent, or Firm* — Hayes Soloway PC

(57) ABSTRACT

A solid-state circadian rhythm lamp and luminaire and related control techniques are disclosed. The lamp or luminaire may have: (1) a night/pre-sleep emissions mode in which it emits light having a correlated color temperature (CCT) of about 1,800-2,300 K, the spectral power ratio of blue light (400-495 nm) being such that it constitutes about 10% or less of the total light emitted; (2) a day/wakeup emissions mode in which it emits light having a CCT of about 5,000-8,000 K, the spectral power ratio of blue light being such that it constitutes about 30% or more of the total light emitted; and/or (3) a general lighting mode in which it produces a combined light output having a CCT of about 2,500-5,000 K. The driver may support emissions mode changing based on hysteresis relating to a lighting switch associated with the lamp or luminaire.

20 Claims, 7 Drawing Sheets

Related U.S. Application Data

(60) Provisional application No. 62/326,200, filed on Apr. 22, 2016.

(51) Int. Cl.
 *A61M 21/02* (2006.01)
 *A61M 21/00* (2006.01)

(52) U.S. Cl.
 CPC .............. *A61N 2005/0652* (2013.01); *A61N 2005/0654* (2013.01); *A61N 2005/0663* (2013.01)

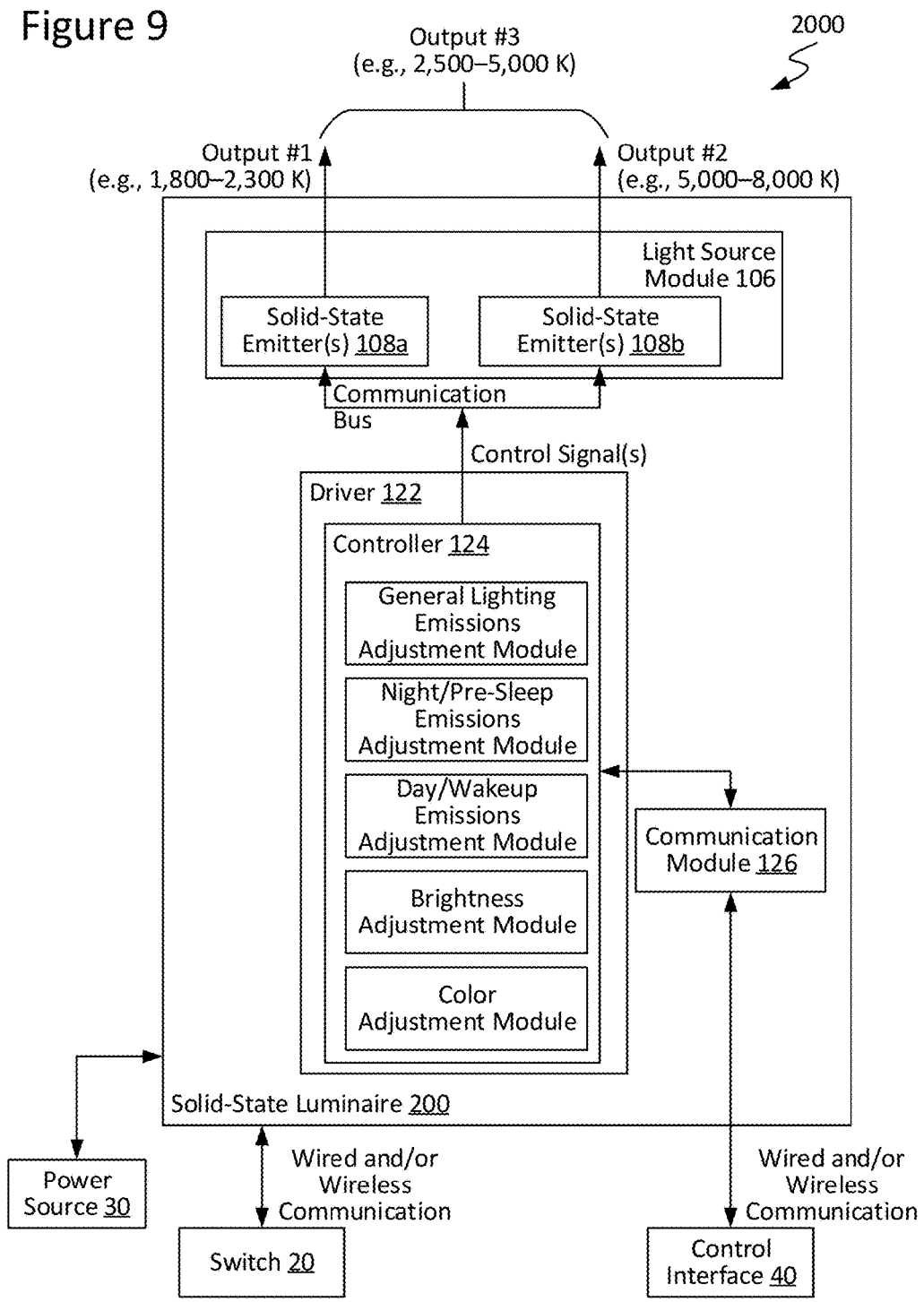

SOLID-STATE CIRCADIAN RHYTHM LAMP AND LUMINAIRE AND RELATED CONTROL TECHNIQUES

CROSS-REFERENCE TO RELATED APPLICATIONS

This patent application is a Continuation-in-Part and claims benefit and priority to U.S. patent application Ser. No. 15/479,882, titled "Solid-State Circadian Rhythm Lamp and Related Control Techniques," filed on Apr. 5, 2017, which claims the benefit of and priority to U.S. Provisional Patent Application No. 62/326,200, titled "Circadian Rhythm Lamp," filed on Apr. 22, 2016, each of which is herein incorporated by reference in its entirety.

FIELD OF THE DISCLOSURE

The present disclosure relates to solid-state lighting (SSL) and more particularly to light-emitting diode (LED)-based lamps and luminaires.

BACKGROUND

Humans and most other living things on Earth exhibit physical, mental, and behavioral changes in response to the presence or absence of light in the surrounding environment throughout the 24-hour cycle of the day. These changes, known as circadian rhythms, can influence sleep/wake cycles and other important bodily functions. In humans, when the body's eyes take in less light at night, the body's suprachiasmatic nucleus (SCN) receives information about the reduction in incoming light and instructs the brain to increase production of the hormone melatonin, normally resulting in drowsiness and eventually sleep. Conversely, as light levels increase in the daytime, the SCN instructs the brain to produce less melatonin, normally resulting in wakefulness and a degree of alertness through the day.

BRIEF DESCRIPTION OF THE DRAWINGS

FIG. 9 illustrates a block diagram of a system including a solid-state luminaire, in accordance with an embodiment of the present disclosure.

Figure 1:
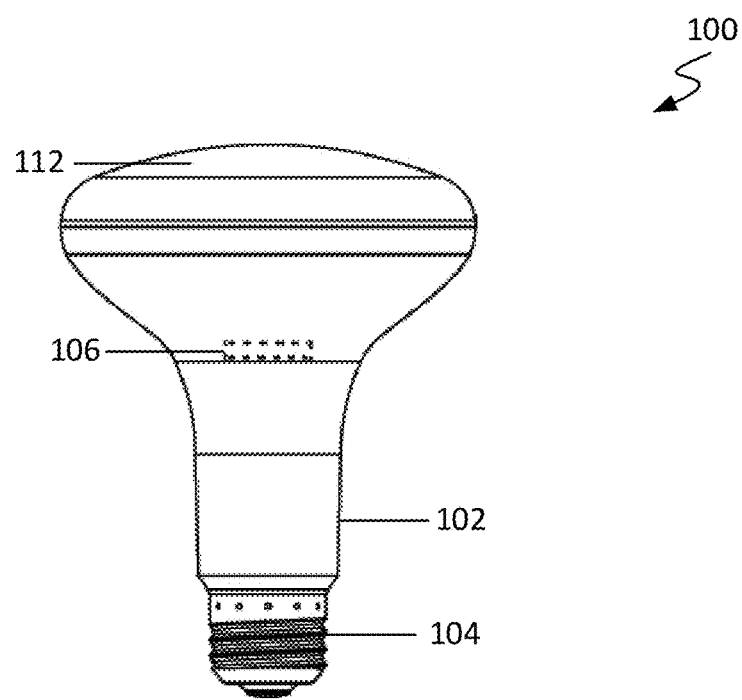
FIG. 1 illustrates a side elevation view of a solid-state lamp configured in accordance with an embodiment of the present disclosure.

These and other features of the present embodiments will be understood better by reading the following detailed description, taken together with the figures herein described. The accompanying drawings are not intended to be drawn to scale. In the drawings, each identical or nearly identical component that is illustrated in various figures may be represented by a like numeral. For purposes of clarity, not every component may be labeled in every drawing.

DETAILED DESCRIPTION

A solid-state circadian rhythm lamp and luminaire and related control techniques are disclosed. In some embodiments, the disclosed lamp or luminaire may have a night/pre-sleep emissions mode in which: (1) a first plurality of emitters emits light having a correlated color temperature (CCT) in the range of about 1,800-2,300 K (ANSI standard); and (2) the spectral power ratio of blue light (400-495 nm) to a remainder of the emitted light is such that the blue light constitutes about 10% or less of the total light emitted. In some embodiments, the lamp or luminaire may have a day/wakeup emissions mode in which: (1) a second plurality of emitters emits light having a CCT in the range of about 5,000-8,000 K (ANSI standard); and (2) the spectral power ratio of blue light (400-495 nm) to a remainder of the emitted light is such that the blue light constitutes about 30% or more of the total light emitted. In some embodiments, the lamp or luminaire may have a general lighting mode in which the first and second pluralities of emitters emit light sequentially at high frequency (e.g., about 2,000 Hz or greater) producing a combined light output having a CCT in the range of about 2,500-5,000 K. In the case of a lamp, switching between emissions modes may be provided by toggling a lighting switch associated with a power socket with which the lamp is coupled, and the driver of the lamp may be configured to support mode changing based on hysteresis relating to the lighting switch. In the case of a luminaire, switching between emissions modes may be provided by toggling a lighting switch associated with the luminaire, and the driver of the luminaire may be configured to support mode changing based on hysteresis relating to the lighting switch. The lighting switch optionally may be native to the luminaire. Numerous configurations and variations will be apparent in light of this disclosure.

General Overview

In humans, a healthy level of melatonin production is directly linked to the quality of natural sleep. Studies indicate that blue light (i.e., light having a wavelength in the range of about 400-495 nm) is closely correlated to melatonin generation in the human body. Thus, exposure to a high level of blue light, for example, right before going to bed may suppress melatonin generation, adversely affecting the quality of sleep. Conversely, exposure to a high level of blue light during the day may help individuals to stay more awake and be more alert, which are attributes important when performing day-to-day physical and mental activities. Thus, varying the blue content of light can help an observer better maintain a natural sleep cycle and improve productivity and performance throughout the day. Traditional incandescent and compact florescent lamps and luminaires, however, are designed to output only one fixed color.

Moreover, dimming is considered an advanced functionality for existing lighting designs, especially for typical compact fluorescent lamps (CFLs).

Thus, and in accordance with some embodiments of the present disclosure, a solid-state circadian rhythm lamp and luminaire and related control techniques are disclosed. In some embodiments, the disclosed lamp or luminaire may have a night/pre-sleep emissions mode in which: (1) a first plurality of emitters emits light having a correlated color temperature (CCT) in the range of about 1,800-2,300 K (ANSI standard); and (2) the spectral power ratio of blue light (400-495 nm) to a remainder of the emitted light is such that the blue light constitutes about 10% or less of the total light emitted. In some embodiments, the lamp or luminaire may have a day/wakeup emissions mode in which: (1) a second plurality of emitters emits light having a CCT in the range of about 5,000-8,000 K (ANSI standard); and (2) the spectral power ratio of blue light (400-495 nm) to a remainder of the emitted light is such that the blue light constitutes about 30% or more of the total light emitted. In some embodiments, the lamp or luminaire may have a general lighting mode in which the first and second pluralities of emitters emit light sequentially at high frequency (e.g., about 2,000 Hz or greater) producing a combined light output having a CCT in the range of about 2,500-5,000 K. In the case of a lamp, switching between emissions modes may be provided by toggling a lighting switch associated with a power socket with which the lamp is coupled, and the driver of the lamp may be configured to support mode changing based on hysteresis relating to the lighting switch. In the case of a luminaire, switching between emissions modes may be provided by toggling a lighting switch associated with the luminaire, and the driver of the luminaire may be configured to support mode changing based on hysteresis relating to the lighting switch. The lighting switch optionally may be native to the luminaire.

As discussed herein, the disclosed lamp and luminaire each may have any of a wide range of emissions modes. In some cases, the lamp or luminaire may be configured with two or three different modes, though additional modes (e.g., four, five, or more) may be provisioned, as desired. Some embodiments may include any one, or combination, of a night/pre-sleep emissions mode, a day/wakeup emissions mode, and a general lighting emissions mode, as discussed herein. The present disclosure is not intended to be so limited, however, as numerous other modes conducive to various target applications and end-uses, such as fitness activities, studying activities, and so forth, may be provisioned, as desired.

As compared to existing daytime and nighttime lamp and luminaire designs, the disclosed lamp and luminaire each may be characterized as having distinctly different emissions characteristics and capabilities that are particularly well-suited for supporting or adjusting circadian rhythms or other physiological processes. For instance, the disclosed lamp and luminaire each may be provided with a lighting profile permitting control over the amount of blue light emitted, which may be used to increase or decrease suppression of melatonin production, thereby affecting sleep processes or other circadian rhythm responses of observers. Thus, in a more general sense, the disclosed lamp and luminaire each may be used, in accordance with some embodiments, to produce specific lighting conditions based on physiological considerations. For instance, before going to sleep, a user may utilize the disclosed lamp or luminaire in night/pre-sleep mode to emit a spectrum having a low blue light content, which may be beneficial to encouraging the onset and maintenance of quality sleep. Also, a user may utilize the disclosed lamp or luminaire in day/wakeup mode to emit a spectrum having a high blue light content, which may expedite waking from sleep and be beneficial to maintaining awareness during the day.

As previously noted, existing lamps and luminaires are normally dedicated only to a single emissions color. Thus, to realize multiple different emissions modes in a target space, multiple different such existing lamps and luminaires, each requiring its own power socket or supply, would need to be employed. This greatly increases system complexity and cost. Contrariwise, a lamp or luminaire provided as described herein may realize multiple emissions modes as a singular lighting component or device utilizing only a single power socket or given power source, as the case may be. Moreover, the disclosed lamp and luminaire each may be compatible with any lighting switch typically used in residential or commercial contexts, providing fast and convenient emissions mode changing with the simple flick of a switch. Thus, contrary to existing lamp and luminaire products, there is no need to invest in a new dimmer switch or gateway or to employ complicated control circuitry or a smartphone and application or other complicated wireless control system to toggle between emissions modes, though any such elements optionally may be utilized in conjunction with the disclosed lamp or luminaire, if desired, in accordance with some embodiments. Furthermore, with the disclosed lamp and luminaire, lighting designers and end-users are offered options to utilize different emissions modes from a single solid-state light source for different target applications or end-uses.

As will be further appreciated in light of this disclosure, the use of solid-state light sources (e.g., LEDs) for circadian rhythm management applications has several advantages compared to traditional incandescent, high-intensity discharge (HID), and fluorescent light sources. For instance, in using solid-state emitters, a lamp or luminaire configured as provided herein may be more energy efficient than existing designs, which may realize a reduction in electricity consumption and operation costs. Also, in using solid-state emitters, a lamp or luminaire configured as provided herein may produce less heat than existing incandescent and HID light sources. Moreover, in using solid-state emitters, a lamp or luminaire configured as provided herein may not require the use of hazardous materials, such as mercury, metal halides, or sodium, contrary to existing fluorescent light and HID light sources.

In accordance with some embodiments, a lamp provided as variously described herein may be configured to be operatively coupled with any of a wide range of luminaires. For instance, in some cases, the disclosed lamp may be compatible with a luminaire configured as a recessed light, a pendant light, a sconce, or the like, which may be mounted on or suspended from, for example, a ceiling, wall, floor, step, or other suitable surface, as will be apparent in light of this disclosure. In some cases, the disclosed lamp may be compatible with a luminaire configured as a free-standing lighting device, such as a desk lamp or torchière lamp. In some embodiments, the disclosed lamp may be compatible with a luminaire configured to be mounted, for example, on a drop ceiling tile (e.g., 1 ft.×1 ft., 2 ft.×2 ft., 2 ft.×4 ft., 4 ft.×4 ft., or larger) for installation in a drop ceiling grid. In some embodiments, the disclosed lamp may be compatible with a luminaire configured, for instance, to substitute for a drop ceiling tile in a drop ceiling grid. In some embodiments, the disclosed lamp may be compatible with a luminaire, such as a downlight can, configured to be mounted onto or into a given mounting surface (e.g., a ceiling, wall, or other structure). Numerous suitable configurations will be apparent in light of this disclosure.

In accordance with some embodiments, a luminaire provided as variously described herein may have any of a wide range of configurations or form factors. For instance, in some cases, the disclosed luminaire may be configured as a recessed light, a pendant light, a sconce, or the like, which may be configured to be mounted on or suspended from, for example, a ceiling, wall, floor, step, or other suitable surface, as will be apparent in light of this disclosure. In some cases, the disclosed luminaire may be configured as a free-standing lighting device, such as a desk lamp or torchière lamp. In some embodiments, the disclosed luminaire may be configured to be mounted, for example, on a drop ceiling tile (e.g., 1 ft.×1 ft., 2 ft.×2 ft., 2 ft.×4 ft., 4 ft.×4 ft., or larger) for installation in a drop ceiling grid. In some embodiments, the disclosed luminaire may be configured, for instance, to substitute for a drop ceiling tile in a drop ceiling grid. In some embodiments, the disclosed luminaire may be configured as a downlight can that is configured to be mounted onto or into a given mounting surface (e.g., a ceiling, wall, or other structure). Numerous suitable configurations will be apparent in light of this disclosure.

In accordance with some embodiments, a luminaire provided as variously described herein may be configured to be operatively coupled with any of a wide range of power sources. For instance, in some cases, the disclosed luminaire may be configured to be operatively coupled with a power source, such as an electrical outlet. In some cases, the disclosed luminaire may be configured to be operatively coupled with a battery. In some instances, a given battery may be integrated with or otherwise hosted by the luminaire or it may be separate from (e.g., non-native to) the luminaire.

Lamp Structure and Operation

Figure 2:
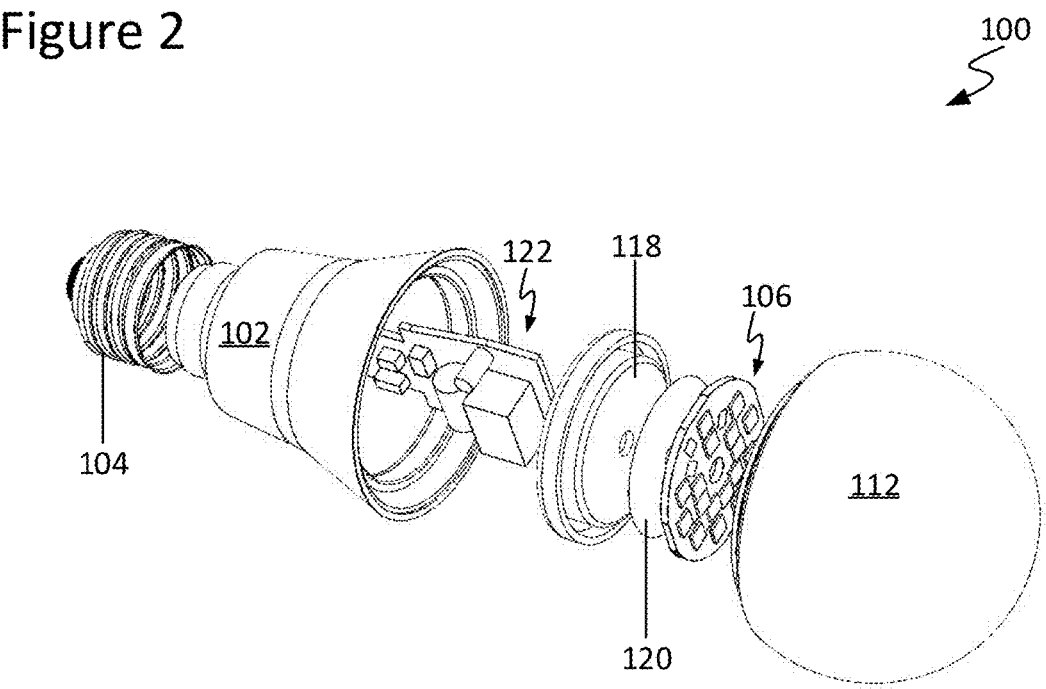
FIG. 2 illustrates an exploded isometric view of a solid-state lamp configured in accordance with an embodiment of the present disclosure.
Figure 3:
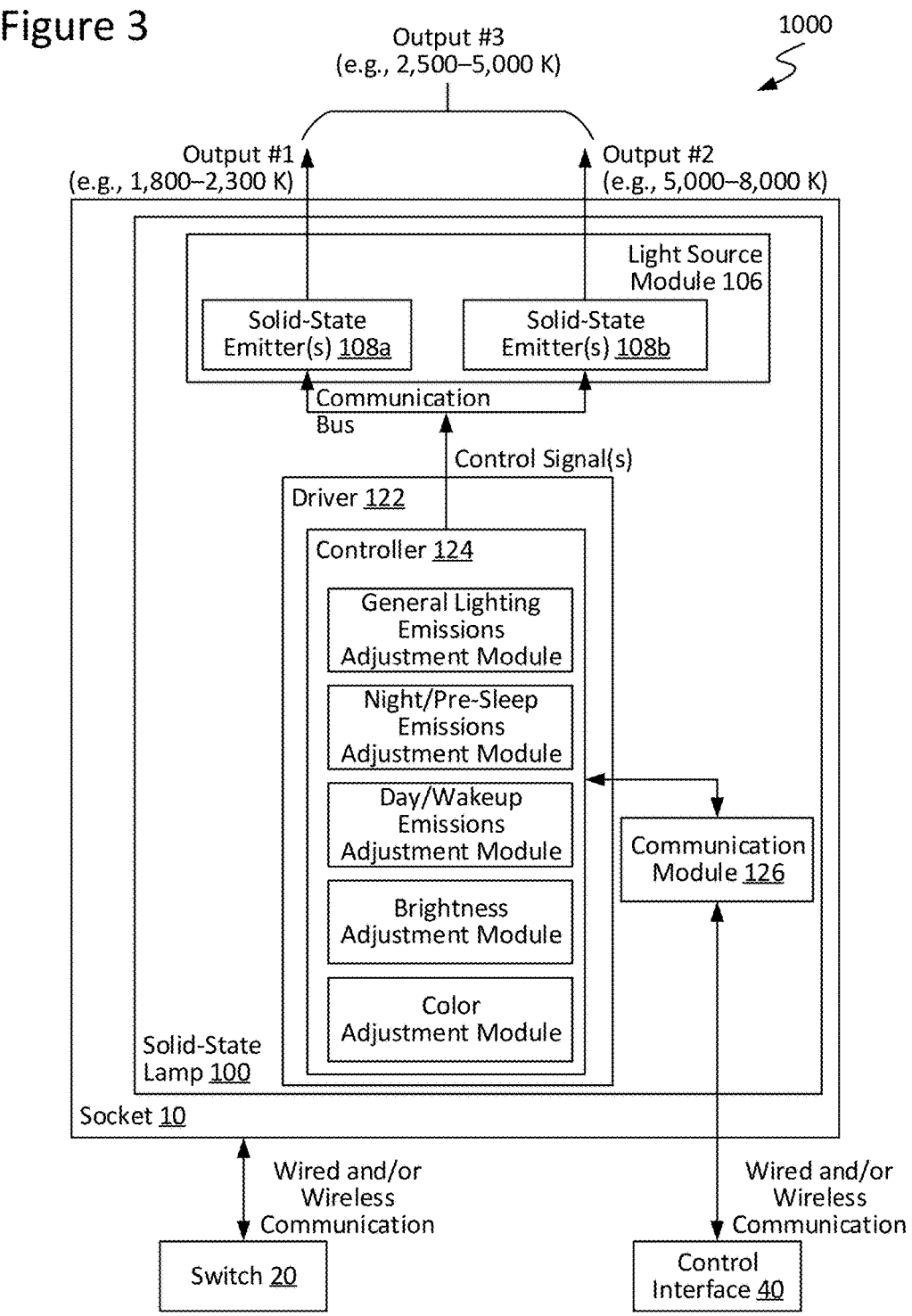
FIG. 3 illustrates a block diagram of a system including a solid-state lamp operatively coupled with a socket, in accordance with an embodiment of the present disclosure.

FIG. 1 illustrates a side elevation view of a solid-state lamp 100 configured in accordance with an embodiment of the present disclosure. FIG. 2 illustrates an exploded isometric view of a solid-state lamp 100 configured in accordance with an embodiment of the present disclosure. FIG. 3 illustrates a block diagram of a system 1000 including a solid-state lamp 100 operatively coupled with a socket 10, in accordance with an embodiment of the present disclosure. As can be seen from these figures, lamp 100 may include a body portion 102, the material, geometry, and dimensions of which may be customized, as desired for a given target application or end-use. Lamp 100 also may include a base portion 104 configured to be operatively coupled with a given power socket 10 so that power may be delivered to lamp 100 for operation thereof. To that end, base portion 104 may be of any standard, custom, or proprietary contact type and fitting size, as desired for a given target application or end-use. In some cases, such as those illustrated in FIGS. 1-2, base portion 104 may be configured as a threaded lamp base including an electrical foot contact (e.g., an Edison-type screw base). In some other cases, base portion 104 may be configured, for example, as a bi-pin, tri-pin, or other multi-pin lamp base, a twist-lock mount lamp base, or a bayonet connector lamp base, to name a few. Other suitable configurations for body portion 102 and base portion 104 will depend on a given application and will be apparent in light of this disclosure.

As will be appreciated in light of this disclosure, lamp 100 may be compatible with power sockets/enclosures typically used in existing luminaire structures. Thus, a lamp 100 configured as variously described herein may be considered, in a general sense, a retrofit or other drop-in replacement lighting component. For example, some embodiments may be of a PAR20, PAR30, PAR38, or other parabolic aluminized reflector (PAR) configuration. Some embodiments may be of a BR30, BR40, or other bulged reflector (BR) configuration. Some embodiments may be of an A19, A21, or other A-line configuration. Some embodiments may be of a T5, T8, or other tube configuration. Some embodiments may be of a retrofit troffer (RT) configuration. Numerous suitable configurations and variations will be apparent in light of this disclosure.

Figure 4:
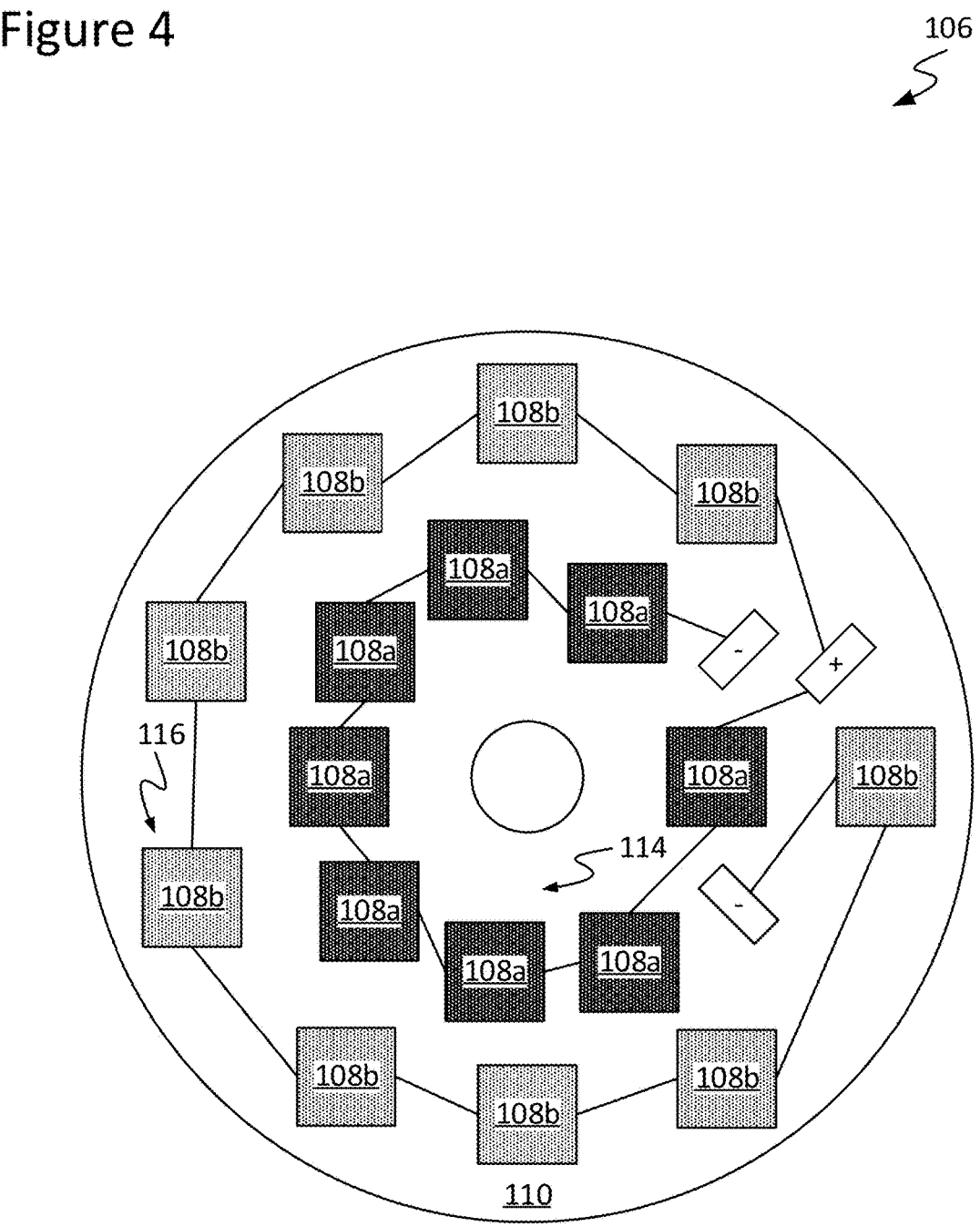
FIG. 4 illustrates a plan view of a light source module configured in accordance with an embodiment of the present disclosure.

As can be seen further from FIGS. 1-3, lamp 100 may include a light source module 106. FIG. 4 illustrates a plan view of a light source module 106 configured in accordance with an embodiment of the present disclosure. As can be seen here, light source module 106 may include one or more solid-state emitters 108a, 108b (collectively referred to as emitters 108, except where separately identified) populated over a printed circuit board (PCB) 110 or other suitable intermediate or substrate. A given emitter 108 may be a semiconductor light source, such as a light-emitting diode (LED), an organic light-emitting diode (OLED), or a polymer light-emitting diode (PLED), among others. In at least one example case, a given emitter 108 may be a 757G LED provided by Nichia Corp. In at least one example case, a given emitter 108 may be a DURIS® LED provided by Osram Sylvania, Inc. Numerous suitable types of emitters 108 will be apparent in light of this disclosure.

Regarding output, a given emitter 108 may be configured to emit electromagnetic radiation (e.g., light) from any one, or combination, of spectral bands, such as, for example, the visible spectral band, the infrared (IR) spectral band, and the ultraviolet (UV) spectral band, among others. A given emitter 108 may be configured for emissions of a single correlated color temperature (CCT) or for color-tunable emissions, as desired. In accordance with some embodiments, emitter(s) 108a may be configured to emit light having a correlated color temperature (CCT) in the range of about 1,800-2,300 K (ANSI standard). In accordance with some embodiments, emitter(s) 108b may be configured to emit light having a CCT in the range of about 5,000-8,000 K (ANSI standard). Other suitable CCT ranges for emitters 108a, 108b will depend on a given application and will be apparent in light of this disclosure.

The electrical power (wattage) of a given emitter 108 may be customized, as desired for a given target application or end-use. In some cases, a given emitter 108 may be a low-power semiconductor light source having a wattage of about 1 W or less (e.g., about 0.25 W or less, about 0.5 W or less, about 0.75 W or less, or any other sub-range in the range of about 1 W or less). In some cases, a given emitter 108 may be a high-power semiconductor light source having a wattage of about 1 W or greater (e.g., about 1.25 W or greater, about 1.5 W or greater, or any other sub-range in the range of about 1 W or greater). Other suitable power output ranges for emitters 108a, 108b will depend on a given application and will be apparent in light of this disclosure.

A given emitter 108 may be electrically coupled with PCB 110 via any suitable standard, custom, or proprietary electrical coupling means, as will be apparent in light of this disclosure. In some cases, PCB 110 further may include other componentry populated there over, such as, for example, resistors, transistors, capacitors, integrated circuits (ICs), and power and control connections for a given emitter 108, to name a few examples. All (or some sub-set) of emitters 108 of light source module 106 may be operatively coupled in series or in parallel (or a combination of both), as desired for a given target application or end-use. In at least one example case, at least one emitter 108 may be of the 6 V variety, though other voltages may be provided, as desired.

The arrangement of emitters 108 over PCB 110 may be customized, as desired for a given target application or end-use. For instance, in some embodiments, emitters 108 may be distributed, in part or in whole, as a regular array in which all (or some sub-set) of emitters 108 are arranged in a systematic manner in relation to one another over PCB 110. In some other embodiments, emitters 108 may be distributed, in part or in whole, as a semi-regular array in which a sub-set of emitters 108 are arranged in a systematic manner in relation to one another over PCB 110, but at least one other emitter 108 is not so arranged. In some other embodiments, emitters 108 may be distributed, in part or in whole, as an irregular array in which all (or some sub-set) of emitters 108 are not arranged in a systematic manner in relation to one another over PCB 110. As generally shown in FIG. 4, emitters 108a may be arranged about the center region of PCB 110, and emitters 108b may be arranged about the perimeter region of PCB 110, at least in some cases. Thus, in a sense, emitters 108b may be arranged concentrically with emitters 108a, in some embodiments. The quantity, density, and spacing between neighboring emitters 108a and 108b over PCB 110 may be customized, as desired for a given target application or end-use.

In accordance with some embodiments, emitters 108 of light source module 106 may be arranged in a single string or in multiple (e.g., two or more) strings. For instance, the example embodiment shown in FIG. 4 includes a first string 114 of emitters 108a and a separate second string 116 of emitters 108b. In at least one example case, first string 114 includes eight emitters 108a, and second string 116 includes nine emitters 108b. Of course, the quantity, density, and spacing between neighboring emitters 108a, 108b for a given string 114, 116 may be customized, and the present disclosure is not intended to be limited only to the example configuration depicted via FIG. 4.

In some cases, for a given string 114, 116, all the constituent emitters 108 thereof may be configured to emit only light of the same single CCT range. In some instances, for a given string 114, 116, a first sub-set of the constituent emitters 108 may be configured to emit light of a first sub-range of a designated CCT range, whereas a second sub-set may be configured to emit light of a different second sub-range of that designated CCT range. In cases where multiple strings (e.g., a first string 114 and a second string 116) are utilized, the forward voltage of the individual emitters 108 may be selected to have the desired voltage difference between strings 114, 116, in accordance with some embodiments.

Returning to FIG. 2, lamp 100 optionally may include a heatsink portion 118 configured to be in thermal communication with light source module 106 to facilitate heat dissipation for lamp 100. To that end, optional heatsink portion 118 may be of monolithic or polylithic construction and formed, in part or in whole, from any suitable thermally conductive material. For instance, optional heatsink portion 118 may be formed from any one, or combination, of aluminum (Al), copper (Cu), gold (Au), brass, steel, or a composite or polymer (e.g., ceramics, plastics, and so forth) doped with thermally conductive material(s). The geometry and dimensions of optional heatsink portion 118 may be customized, as desired for a given target application or end-use. In some instances, a thermal interfacing layer 120 (e.g., a thermally conductive tape or other medium) optionally may be disposed between heatsink portion 118 and light source module 106 to facilitate thermal communication there between. Other suitable configurations for optional heatsink portion 118 and optional thermal interfacing layer 120 will depend on a given application and will be apparent in light of this disclosure.

As can be seen further from FIGS. 2-3, lamp 100 may include a driver 122, which may be disposed within body portion 102 or other portion of lamp 100. Driver 122 may be a single-channel or multi-channel electronic driver configured to drive emitter(s) 108 utilizing pulse-width modulation (PWM) dimming or any other suitable standard, custom, or proprietary driving techniques, as will be apparent in light of this disclosure. As further shown in FIG. 3, driver 122 may include a controller 124. In accordance with some embodiments, driver 122 may be configured to provide lamp 100 with two-mode operation; that is, driver 122 may provide lamp 100 with: (1) a first emissions mode in which it emits light having a first CCT; and (2) a second emissions mode in which it emits light having a different second CCT. To this end, controller 124 may be, for example, an OZ2082C LED driver controller provided by O₂Micro International Ltd. In accordance with some other embodiments, driver 122 may be configured to provide lamp 100 with three-mode operation; that is, driver 122 may provide lamp 100 with first and second emissions modes (as previously discussed), as well as a third emissions mode in which it emits light of both the first CCT and the second CCT, which combine to provide light having a different third CCT. To this end, controller 124 may be, for example, an OZ2093 FREE-DIMMING™ LED driver controller provided by O₂Micro International Ltd.

Note, however, that the present disclosure is not intended to be limited only to drivers 122 including these specific example controllers 124. In a more general sense, and in accordance with some other embodiments, controller 124 can be any power supply controller IC or microcontroller having the ability to sense the operation of the input power (e.g., based on the on/off state of switch 20, discussed below) while maintaining a hysteresis from on-to-off and off-to-color control, with color control being provided by controlling the on/off state of emitter(s) 108a and 108b. In some still other cases, controller 124 may be a microcontroller programmed to receive a control input from a wired or wireless source other than, or in addition to, a switch (e.g., such as switch 20) and accordingly generate a target CCT by controlling the duty cycle of strings 114, 116.

In two-mode, three-mode, or other multi-mode operation, lamp 100 may be driven by driver 122 including a controller 124 configured to support mode changing for lamp 100 based, in part or in whole, on hysteresis. In accordance with some embodiments, the output of emitter(s) 108 and thus lamp 100 may be electronically controlled by controller 124. To such ends, controller 124 may be operatively coupled with emitter(s) 108 (or light source module 106 more generally), for instance, by a communication bus or other suitable interconnect. Controller 124 may be configured to communicate with emitter(s) 108 via any one, or combination, of suitable standard, custom, or proprietary wired or wireless digital communications protocols, as will be apparent in light of this disclosure.

Controller 124 may be configured to electronically control emitters 108 to provide lamp 100 with highly adjustable light emissions. In some instances, color control may be provided by controlling strings 114, 116, with only one string conducting at a time, thereby providing two-mode operation. In some other instances, color control may implement high-frequency switching between strings 114, 116, thereby providing three-mode operation. To such ends, controller 124 may host one or more lighting control modules and may be programmed or otherwise configured to output one or more control signals that may be utilized in controlling the operation of a given emitter 108 of lamp 100. For instance, in some embodiments, controller 124 may include a night/pre-sleep emissions adjustment module and may be configured to output control signal(s) to adjust characteristics of light emitted by emitter(s) 108*a* having a CCT in the range of about 1,800-2,300 K. In some embodiments, controller 124 may include a day/wakeup emissions adjustment module and may be configured to output control signal(s) to adjust characteristics of light emitted by emitter(s) 108*b* having a CCT in the range of about 5,000-8,000 K. In some embodiments, controller 124 may include a general lighting emissions adjustment module and may be configured to output control signal(s) to adjust characteristics of light emitted by emitter(s) 108*a* and emitter(s) 108*b* to achieve a combined/mixed output of light having a CCT in the range of about 2,500-5,000 K. In some embodiments, controller 124 may include a brightness adjustment module and may be configured to output control signal(s) to control the intensity (e.g., brightness or dimness) of the light emitted by a given emitter 108. In some embodiments, controller 124 may include a color adjustment module and may be configured to output control signal(s) to control the color (e.g., wavelength) of the light emitted by a given emitter 108. In some embodiments, controller 124 may be configured to output control signal(s) for use in controlling whether a given emitter 108 is in an on state or an off state. Note, however, that the present disclosure is not intended to be limited only to these example lighting control modules and output signals; additional and/or different lighting control modules and output signals may be provisioned, as desired for a given target application or end-use.

In accordance with some embodiments, the module(s) of controller 124 may be implemented in any suitable standard, custom, or proprietary programming language, such as, for example, C, C++, objective C, JavaScript, or any other suitable instruction set, as will be apparent in light of this disclosure. The module(s) of controller 124 can be encoded, for example, on a machine-readable medium that, when executed by a processor, carries out the functionality of lamp 100, in part or in whole. The computer-readable medium may be, for example, a hard drive, a compact disk, a memory stick, a server, or any suitable non-transitory computer or computing device memory that includes executable instructions, or a plurality or combination of such memories. Some embodiments can be implemented, for instance, with gate-level logic, an application-specific integrated circuit (ASIC) or chip set, or other such purpose-built logic. Some embodiments can be implemented with a microcontroller having input/output capability (e.g., inputs for receiving user inputs; outputs for directing other components) and embedded routines for carrying out device functionality. In a more general sense, the functional modules of controller 124 can be implemented in any one, or combination, of hardware, software, and firmware, as desired for a given target application or end-use. Moreover, in some embodiments, a given module of controller 124 (or controller 124 more generally) may be programmable to achieve any of the various functions and emissions capabilities desired of lamp 100 for a given target application or end-use.

As will be appreciated in light of this disclosure, lamp 100 further may include or otherwise have access to any of a wide range of other electronic components employable with solid-state lamps and luminaires. For instance, in some embodiments, lamp 100 may include or otherwise have access to power conversion componentry, such as electrical ballast circuitry, configured to convert an AC signal into a DC signal at a desired current/voltage to power a given light source module 106. In some instances, lamp 100 may include self-ballasted electronics (e.g., disposed within base portion 104 or other portion of lamp 100). In some embodiments, lamp 100 may include or otherwise have access to processing componentry, such as a central processing unit (CPU) or a microcontroller unit (MCU), among others.

Returning to FIGS. 1-2, lamp 100 also may include one or more optics 112, which may have any of a wide range of configurations. A given optic 112 may be configured to transmit, in part or in whole, emissions received from a given emitter 108 optically coupled therewith, in accordance with some embodiments. A given optic 112 may be formed from any one, or combination, of suitable optical materials. For instance, in some embodiments, a given optic 112 may be formed from a polymer, such as poly(methyl methacrylate) (PMMA) or polycarbonate, among others. In some embodiments, a given optic 112 may be formed from a ceramic, such as sapphire ($Al_2O_3$) or yttrium aluminum garnet (YAG), among others. In some embodiments, a given optic 112 may be formed from a glass. In some embodiments, a given optic 112 may be formed from a combination of any of the aforementioned materials. Furthermore, the dimensions and geometry of a given optic 112 may be customized, as desired for a given target application or end-use. In some embodiments, a given optic 112 may be or otherwise include a lens, such as a Fresnel lens, a converging lens, a compound lens, or a micro-lens array, to name a few. In some embodiments, a given optic 112 may be or otherwise include an optical dome or optical window. In some cases, a given optic 112 may be formed as a singular piece of optical material, providing a monolithic optical structure. In some other cases, a given optic 112 may be formed from multiple pieces of optical material, providing a polylithic (multi-piece) optical structure. In some instances, a given optic 112 may be configured to filter light transmitted therethrough. Other suitable configurations for optic(s) 112 will depend on a given application and will be apparent in light of this disclosure.

As previously discussed, lamp 100 may be configured with a plurality of emissions modes. For instance, in accordance with some embodiments, lamp 100 may have a nighttime/pre-sleep emissions mode in which only emitter(s) 108*a* having a CCT in the range of about 1,800-2,300 K may be turned on and emitting light. Furthermore, in this emissions mode, the spectral power ratio of light having a wavelength in the range of about 400-495 nm (e.g., generally blue light) to light emitted in a remainder of the emitted spectrum may be such that the blue light constitutes about 10% or less (e.g., about 8% or less, about 5% or less, about 3% or less, or any other sub-range in the range of about 10% or less) of the total light emitted by lamp 100. In at least some instances, light of this CCT range and spectral power ratio may be conducive to inducing and maintaining sleep. As will be appreciated in light of this disclosure, it may be desirable, in a general sense, to minimize the blue light content of the emissions of lamp 100 (e.g., reduce as close to 0% blue light as possible), as well as lower the intensity of the output, in night/pre-sleep emissions modes.

In accordance with some embodiments, lamp 100 may have a daytime/wakeup emissions mode in which only emitter(s) 108*b* having a CCT in the range of about 5,000-8,000 K may be turned on and emitting light. Furthermore, in this emissions mode, the spectral power ratio of light having a wavelength in the range of about 400-495 nm (e.g., generally blue light) to light emitted in a remainder of the emitted spectrum may be such that the blue light constitutes about 30% or more (e.g., about 35% or more, about 40% or more, about 45% or more, about 50% or more, or any other sub-range in the range of about 30% or more) of the total light emitted by lamp 100. In at least some instances, light of this CCT range and spectral power ratio may be conducive to inducing and maintaining a state of wakefulness/alertness. As will be appreciated in light of this disclosure, it may be desirable, in a general sense, to maximize the blue light content of the emissions of lamp 100 (e.g., increase as high as possible while still maintaining levels physically safe to an observer), as well as increase the intensity of the output, in day/wakeup emissions modes.

Figure 5:
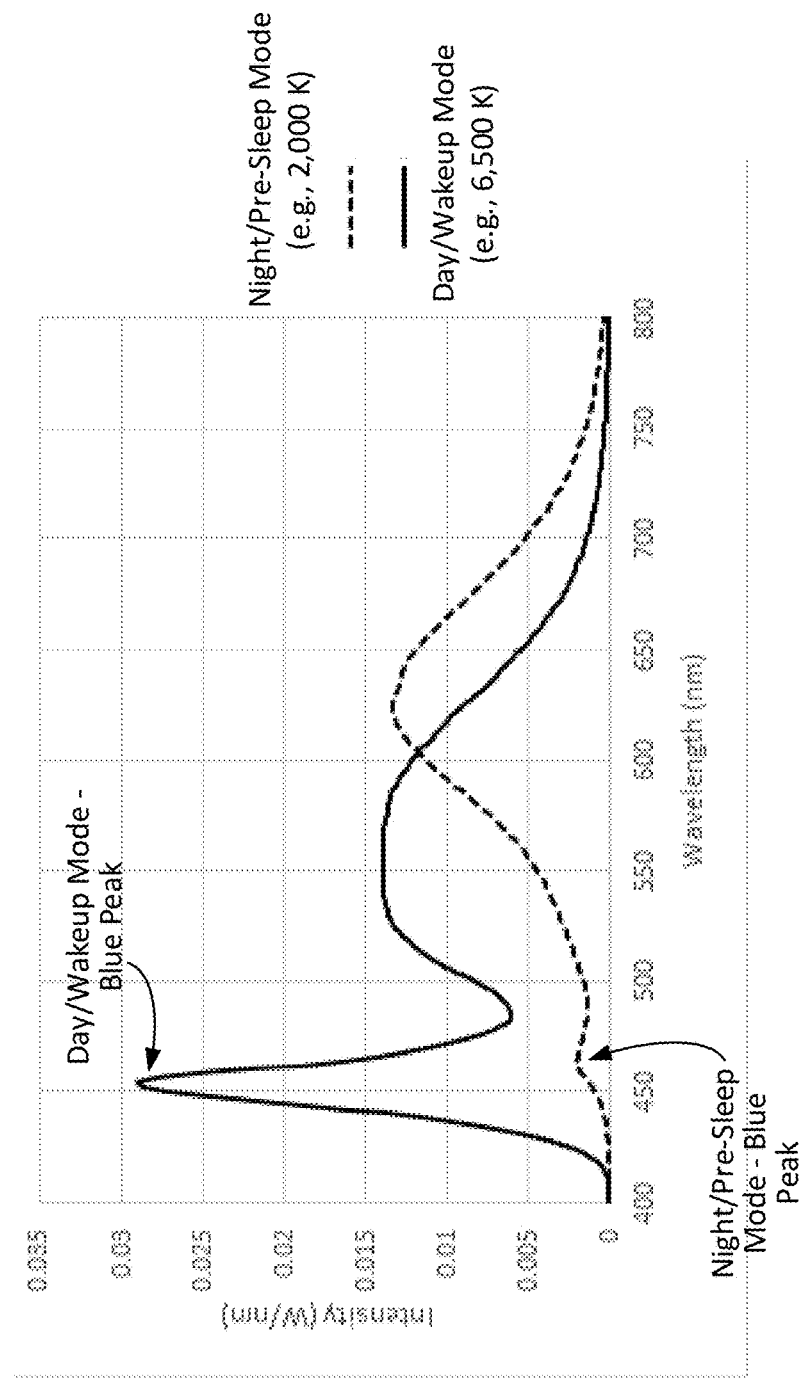
FIG. 5 is a graph illustrating spectral power distribution (SPD) of a solid-state lamp configured with a night/pre-sleep mode and a day/wakeup mode in accordance with an embodiment of the present disclosure.

FIG. 5 is a graph illustrating spectral power distribution (SPD) of a lamp 100 configured with a night/pre-sleep mode and a day/wakeup mode in accordance with an embodiment of the present disclosure. As can be seen here, in a night/pre-sleep emissions mode having a CCT of about 2,000 K, the spectral power ratio of blue light (e.g., light with a wavelength of between about 400-495 nm) to the total emitted spectral region is less than or equal to about 10% (e.g., about 7.5-10%, about 7.5% or less, about 5-7.5%, about 5% or less, about 2.5-5%, about 2.5% or less, about 0.1-2.5%, or any other sub-range in the range of less than or equal to about 10%). Moreover, in this example emissions mode, there is a relatively small peak in the blue light region of the emissions spectrum, and the spectral power ratio between that blue peak and the total emitted spectral region is around 4.8%. As can be seen further from FIG. 5, in a day/wakeup emissions mode having a CCT of about 6,500 K, the spectral power ratio of blue light (e.g., light with a wavelength of between about 400-495 nm) to the total emitted spectral region is greater than or equal to about 30% (e.g., about 30-40%, about 40% or more, about 40-50%, about 50% or more, about 50-60%, about 60% or more, or any other sub-range in the range of greater than or equal to about 30%). Moreover, in this example emissions mode, there is a relatively large peak in the blue light region of the emissions spectrum, and the spectral power ratio of that blue peak to the total emitted spectral region is around 48.1%.

In accordance with some embodiments, lamp 100 may have one or more general lighting emissions modes in which emitter(s) 108a (having a CCT in the range of about 1,800-2,300 K) and emitter(s) 108b (having a CCT in the range of about 5,000-8,000 K) may be turned on and off sequentially at high frequency and emitting light. The resultant combined light output may have a CCT in the range of about 2,500-5,000 K (e.g., about 2,500-3,000 K, about 3,000-3,500 K, about 3,500-4,000 K, about 4,000-4,500 K, about 4,500-5,000 K, or any other sub-range in the range of about 2,500-5,000 K). In some instances, lamp 100 may include only a single general lighting emissions mode in which it emits a combined light output of a single CCT or single range of CCTs. In other instances, multiple general lighting emissions modes may be provisioned for lamp 100. For example, in a first general lighting emissions mode, lamp 100 may emit a combined light output having a first CCT or first range of CCTs, whereas in a second general lighting emissions mode, lamp 100 may emit a combined light output having a different second CCT or different second range of CCTs. Any quantity of general lighting emissions modes may be provided, as desired, and emissions blending for emitter(s) 108a and 108b may be customized to achieve given target output CCT value(s).

Figure 6:
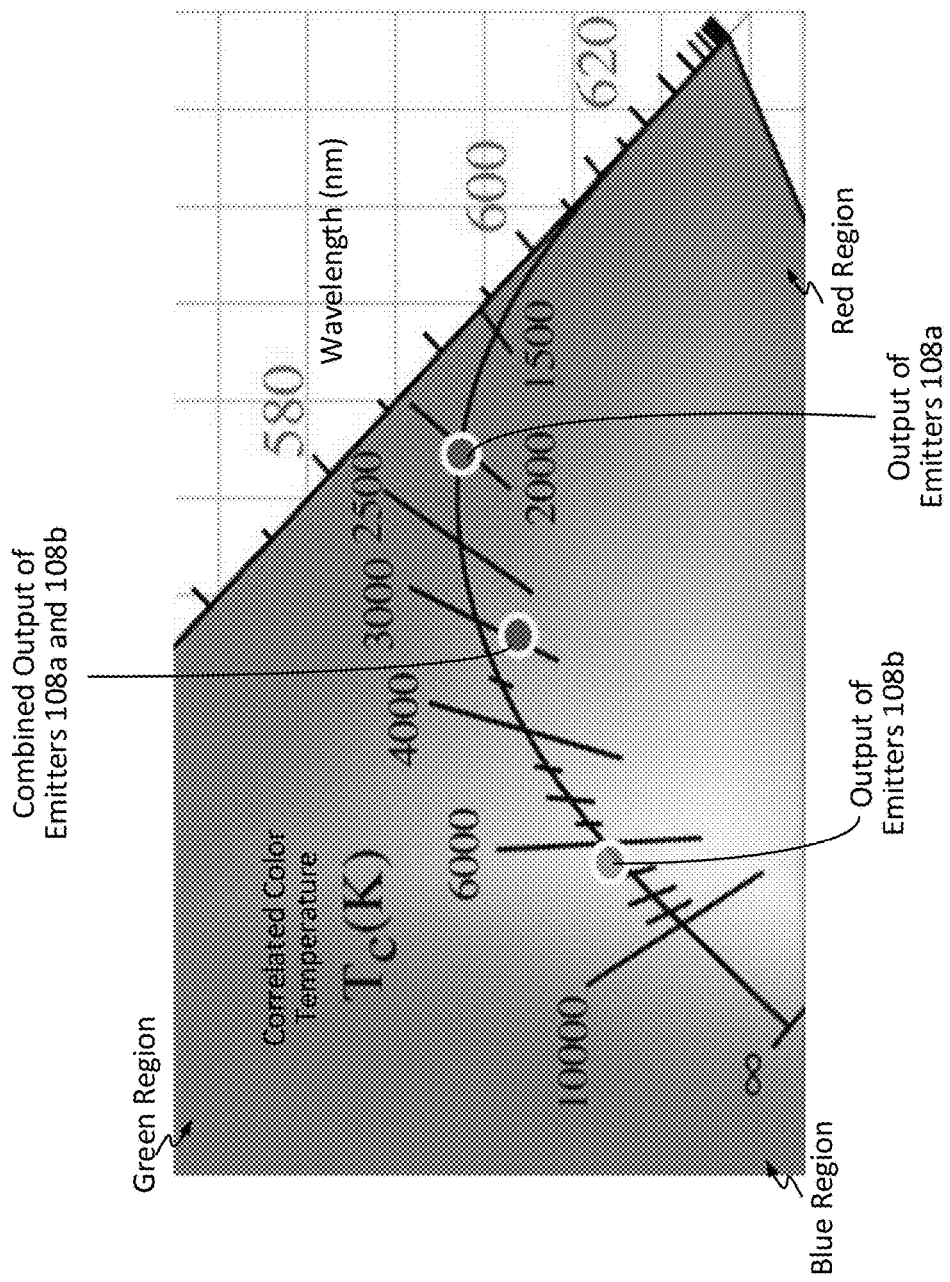
FIG. 6 is a color point graph illustrating color mixing of emitters of a solid-state lamp, in accordance with an embodiment of the present disclosure.

FIG. 6 is a color point graph illustrating color mixing of emitter(s) 108a and emitter(s) 108b of lamp 100 in accordance with an embodiment of the present disclosure. As can be seen here, by mixing output of emitter(s) 108a with output of emitter(s) 108b, a combined output having a CCT in the range of about 2,500-5,000 K may be provided. To this end, driver 122 may control emitter(s) 108a via PWM (or other suitable technique) to account for about 50%-75% (e.g., about 70%±5%, or any other sub-range in the range of about 50%-75%) of the emitted light of lamp 100, in accordance with some embodiments. Correspondingly, driver 122 may control emitter(s) 108b via PWM (or other suitable technique) to account for about 25%-50% (e.g., about 30%±5%, or any other sub-range in the range of about 25%-50%) of the emitted light of lamp 100, in accordance with some embodiments. In this general lighting emissions mode, lamp 100 may be configured to have only either emitter(s) 108a or emitter(s) 108b on at a given time. Thus, while string 114 may be turned on and emitting light, string 116 may be turned off, and vice-versa. The frequency of turning strings 114, 116 on and off with respect to one another may be customized, as desired, and may be sufficiently high to be imperceptible to an observer.

Figure 7:
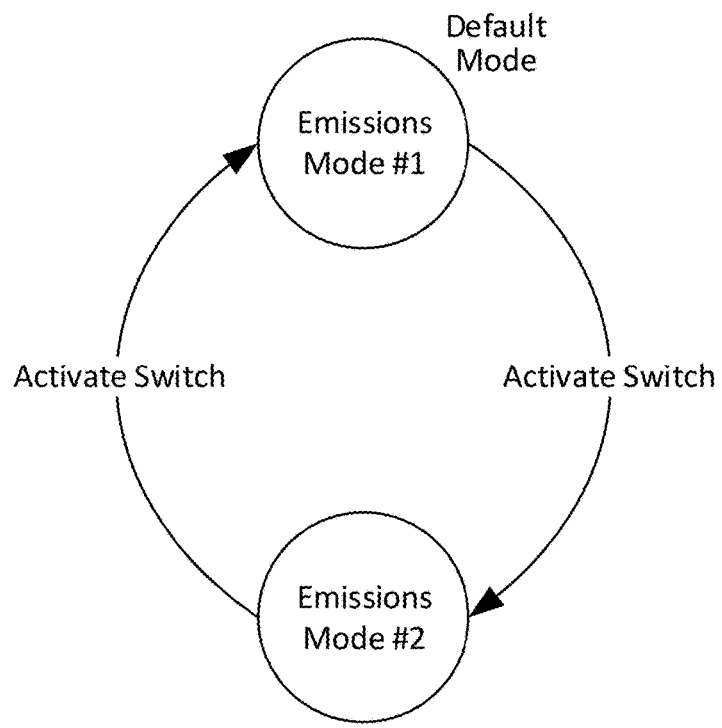
FIG. 7 is a state diagram illustrating the transitions of a two-mode lamp configured in accordance with an embodiment of the present disclosure.

In accordance with some embodiments, lamp 100 may be configured with two different emissions modes. FIG. 7 is a state diagram illustrating the transitions of a two-mode lamp 100 configured in accordance with an embodiment of the present disclosure. As can be seen here, when initially turned on, lamp 100 may start in a first emissions mode. This first emissions mode may be designated (e.g., by a user or otherwise) as the default mode for that lamp 100, at least in some instances. Lamp 100 then may be transitioned from the first emissions mode to a different second emissions mode, for instance, by activating a switch 20 (discussed below). To these ends, driver 122 may be customized, as desired, and in at least some embodiments may include as controller 124 an OZ2082C LED driver controller provided by O₂Micro International Ltd., as previously discussed. Table 1 below lists various cycling combinations of emissions modes for two-mode lamps 100 configured in accordance with some embodiments of the present disclosure:

TABLE 1

| Emissions Mode #1 (Default Mode) | Emissions Mode #2 |
|---|---|
| Night/Pre-Sleep | Day/Wakeup |
| Night/Pre-Sleep | General Lighting |
| Day/Wakeup | Night/Pre-Sleep |
| Day/Wakeup | General Lighting |
| General Lighting | Night/Pre-Sleep |
| General Lighting | Day/Wakeup |

Figure 8:
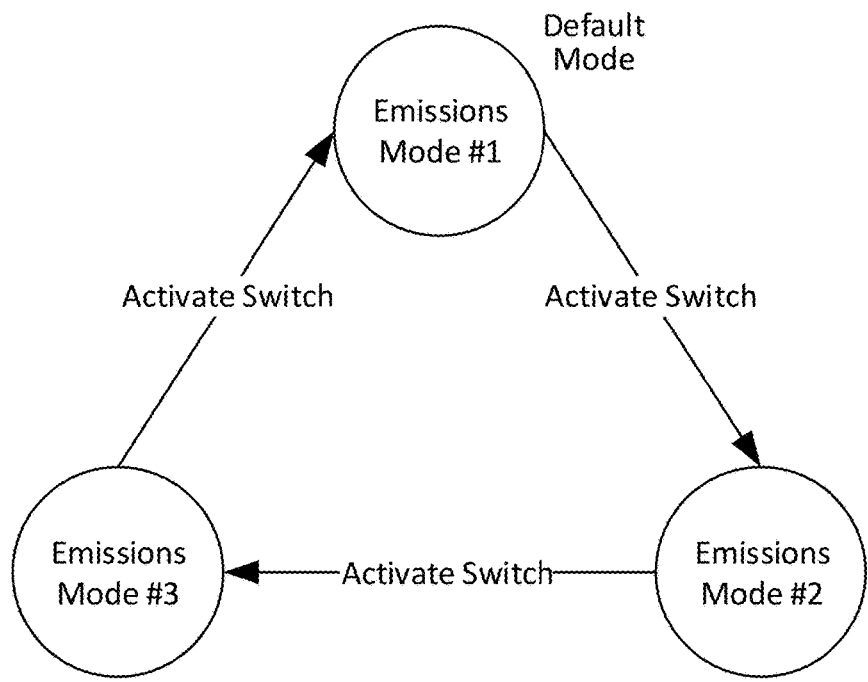
FIG. 8 is a state diagram illustrating the transitions of a three-mode lamp configured in accordance with an embodiment of the present disclosure.

In accordance with some other embodiments, lamp 100 may be configured with three different emissions modes. FIG. 8 is a state diagram illustrating the transitions of a three-mode lamp 100 configured in accordance with an embodiment of the present disclosure. As can be seen here, when initially turned on, lamp 100 may start in a first emissions mode. As previously discussed, the first emissions mode may be designated (e.g., by a user or otherwise) as the default mode for that lamp 100, at least in some instances. Lamp 100 then may be transitioned from the first emissions mode to a different second emissions mode, for instance, by activating a switch 20 (discussed below). Thereafter, lamp 100 may be transitioned from the second emissions mode to a different third emissions mode, for instance, by activating switch 20. To these ends, driver 122 may be customized, as desired, and in at least some embodiments may include as controller 124 an OZ2093 FREE-DIMMING™ LED driver controller provided by O₂Micro International Ltd., as previously discussed. Table 2 below lists various cycling combinations of emissions modes for three-mode lamps 100 configured in accordance with some embodiments of the present disclosure:

TABLE 2

| Emissions Mode #1 (Default Mode) | Emissions Mode #2 | Emissions Mode #3 |
|---|---|---|
| Night/Pre-Sleep | General Lighting | Day/Wakeup |
| Night/Pre-Sleep | Day/Wakeup | General Lighting |
| Day/Wakeup | General Lighting | Night/Pre-Sleep |
| Day/Wakeup | Night/Pre-Sleep | General Lighting |
| General Lighting | Night/Pre-Sleep | Day/Wakeup |
| General Lighting | Day/Wakeup | Night/Pre-Sleep |

In accordance with some embodiments, changing of the emissions modes of lamp 100 may be performed by operating a lighting switch 20 communicatively coupled with a socket 10 with which lamp 100 is operatively coupled. More specifically, by flicking switch 20, lamp 100 may cycle through its various emissions modes. To such ends, switch 20 may be, for example, a toggle light switch or rocker switch, configured as typically done, or any other suitable household or commercial type of lighting switch, as will be apparent in light of this disclosure.

When lamp 100 is turned on initially by toggling switch 20 into its on position, lamp 100 may enter its first emissions mode. If lamp 100 is then turned off (by toggling switch 20 into its off position) and on again (by toggling switch 20 into its on position) within a specified first time window, lamp 100 may enter its second emissions mode. If lamp 100 is thereafter turned off again (by toggling switch 20 into its off position) and on again (by toggling switch 20 into its on position) within a specified second time window, lamp 100 either may: (1) return to the first emissions mode, if lamp 100 is a two-mode lamp; or (2) enter its third emissions mode, if lamp 100 is a three-mode lamp. The duration of each of the first and second time windows may be customized, as desired, and in at least some cases may be about 3 seconds or less (e.g., about 2.5 seconds or less, about 2 seconds or less, about 1.5 seconds or less, about 1 second or less, or any other sub-range in the range of about 3 seconds or less). In some cases, the first and second time windows may be of the same duration, whereas in other cases, those windows may differ in duration. In some instances, either (or both) the first and second time windows may be user-programmable.

Returning to FIG. 3, lamp 100 optionally may include a communication module 126, which may be configured as a transmitter, a receiver, or both (i.e., a transceiver). In some cases, communication module 126 may be separate and distinct from controller 124 (e.g., as generally shown in FIG. 3), though in some other cases, communication module 126 may be a component of or otherwise integrated with controller 124. In accordance with some embodiments, controller 124 may be configured to output control signal(s) to emitter(s) 108 based, at least in part, on input received from a remote source, such as a control interface 40. Control interface 40 may be physical, virtual, or a combination thereof and may be configured to communicate with controller 124 (via intervening communication module 126), which in turn interprets input received from control interface 40 and distributes desired control signal(s) to emitter(s) 108 of light source module 106. Control interface 40 may be employed, in accordance with some embodiments, in changing the emissions modes of lamp 100. To such ends, communication module 126 and control interface 40 may be configured for wired or wireless communication (or both) utilizing any one, or combination, of suitable means, such as Universal Serial Bus (USB), Ethernet, FireWire, Wi-Fi, Bluetooth, or ZigBee, among others. Optionally, control interface 40 may be or otherwise employ a touch-sensitive display or surface, such as a touchpad or other device with a touch-based user interface (UI) or graphical UI (GUI), as provided by a computing device, mobile or otherwise. Other suitable configurations for communication module 126 and control interface 40 will depend on a given application and will be apparent in light of this disclosure.

Luminaire Structure and Operation

FIG. 9 illustrates a block diagram of a system 2000 including a solid-state luminaire 200, in accordance with an embodiment of the present disclosure. As can be seen, luminaire 200 may include any one, or combination, of the various components, features, and capabilities discussed above, for instance, with respect to lamp 100 (e.g., in relation to FIGS. 1-4), in accordance with some embodiments. As will be appreciated in light of this disclosure, any of the various components, features, and capabilities discussed above in relation to system 1000 and its constituents, including lamp 100, for instance, may be integrated with or otherwise hosted by luminaire 200, in part or in whole, or may be separate from (e.g., non-native to) luminaire 200, in part or in whole, in accordance with some embodiments. As will be further appreciated, luminaire 200 may be configured, in accordance with some embodiments, such that it has an SPD like that discussed above with respect to lamp 100 (e.g., in relation to FIG. 5). Also, as will be appreciated, luminaire 200 may be configured, in accordance with some embodiments, such that it has color mixing like that discussed above with respect to lamp 100 (e.g., in relation to FIG. 6). Furthermore, as will be appreciated, luminaire 200 may be configured, in accordance with some embodiments, such that it operates in various modes like those discussed above with respect to lamp 100 (e.g., in relation to FIGS. 7-8).

In accordance with some embodiments, luminaire 200 may be constructed, in part or in whole, from any of a wide range of materials. For instance, in accordance with some embodiments, luminaire 200 may be constructed from any one, or combination, of: aluminum (Al); copper (Cu); brass; steel (e.g., stainless steel or other steel); or a composite or polymer (e.g., ceramics, plastics, etc.), optionally doped with thermally conductive material(s). The size and geometry of luminaire 200 may be customized, as desired for a given target application or end-use.

In accordance with some embodiments, luminaire 200 may be configured to be mounted on or otherwise fixed to a mounting surface in a temporary or permanent manner. In some cases, luminaire 200 may be configured to be mounted as a recessed lighting fixture, while in some other cases, luminaire 200 may be configured as a pendant-type fixture, a sconce-type fixture, or other lighting fixture which may be suspended or otherwise extended from a given mounting surface. Some example suitable mounting surfaces include ceilings, walls, floors, and/or steps. In some instances, the mounting surface may be a drop ceiling tile (e.g., having an area of about 2 ft.×2 ft., 2 ft.×4 ft., 4 ft.×4 ft., etc.) for installment in a drop ceiling grid. However, it should be noted that luminaire 200 need not be configured to be mounted on a mounting surface and instead may be configured, in some instances, as a free-standing or otherwise portable lighting device, such as a desk lamp or a torchière lamp, for example. Other suitable configurations will depend on a given application and will be apparent in light of this disclosure.

As previously noted, luminaire 200 optionally may be configured to be operatively coupled with a power source 30 so that power may be delivered to luminaire 200 for operation thereof. In some embodiments, power source 30 may be integrated with or otherwise hosted by luminaire 200. In some other embodiments, however, power source 30 may be separate from (e.g., non-native to) luminaire 200. In some cases, power source 30 may be an electrical outlet, which may be configured as typically done. In some cases, power source 30 may be a battery, which may be permanent or replaceable. In some cases, power source 30 may include or be operatively coupled with a photovoltaic module (e.g., a solar cell) configured to convert light energy to electrical energy for use by luminaire 200. Other suitable configurations for power source 30 will depend on a given application and will be apparent in light of this disclosure.

In accordance with some embodiments, changing of the emissions modes of luminaire 200 may be performed by operating a lighting switch 20 (or other switch, native to luminaire 200 or otherwise) communicatively coupled with luminaire 200. More specifically, by flicking switch 20 (or other switch), luminaire 200 may cycle through its various emissions modes. As will be appreciated, entering and cycling through the one or more emissions modes of luminaire 200 may be provided in a manner like that discussed above, for instance, with respect to lamp 100, in accordance with some embodiments.

Numerous embodiments will be apparent in light of this disclosure. One example embodiment provides a solid-state luminaire including: a printed circuit board (PCB); a first plurality of solid-state emitters populated over the PCB and configured to emit light having a first correlated color temperature (CCT); a second plurality of solid-state emitters populated over the PCB and configured to emit light having a second CCT that differs from the first CCT. The solid-state luminaire further includes a controller configured to: electronically control, via a control signal, emissions of the first plurality of solid-state emitters and the second plurality of solid-state emitters such that: in a first emissions mode, the first plurality of solid-state emitters emits light, wherein a spectral power ratio of the light emitted at a wavelength in the range of about 400-495 nm to a remainder of the light emitted by the first plurality of solid-state emitters in the first emissions mode is such that the light emitted at the wavelength in the range of about 400-495 nm constitutes about 10% or less of a total light emitted by the first plurality of solid-state emitters; and in a second emissions mode, the second plurality of solid-state emitters emits light, wherein a spectral power ratio of the light emitted at a wavelength in the range of about 400-495 nm to a remainder of the light emitted by the second plurality of solid-state emitters in the second emissions mode is such that the light emitted at the wavelength in the range of about 400-495 nm constitutes about 30% or more of a total light emitted by the second plurality of solid-state emitters; and provide for changing between the first emissions mode and the second emissions mode based on hysteresis of a lighting switch associated with the solid-state luminaire. In some cases: the first CCT is in the range of about 1,800-2,300 K; and the spectral power ratio of the light emitted at a wavelength in the range of about 400-495 nm to the remainder of the light emitted by the first plurality of solid-state emitters in the first emissions mode is such that the light emitted at the wavelength in the range of about 400-495 nm constitutes about 5% or less of the total light emitted by the first plurality of solid-state emitters. In some cases: the second CCT is in the range of about 5,000-8,000 K; and the spectral power ratio of the light emitted at a wavelength in the range of about 400-495 nm to the remainder of the light emitted by the second plurality of solid-state emitters in the second emissions mode is such that the light emitted at the wavelength in the range of about 400-495 nm constitutes about 40% or more of the total light emitted by the second plurality of solid-state emitters. In some instances, in providing for changing between the first emissions mode and the second emissions mode based on hysteresis of the lighting switch, the controller is configured such that: in turning on the solid-state luminaire by toggling the lighting switch from an off position to an on position, the solid-state luminaire enters the first emissions mode; and in turning off the solid-state luminaire by toggling the lighting switch from the on position to the off position and then turning on the solid-state luminaire again by toggling the lighting switch from the off position to the on position within a time window of about 3 seconds or less, the solid-state luminaire transitions from the first emissions mode to the second emissions mode. In some instances, the controller is further configured to: electronically control, via the control signal, emissions of both the first plurality of solid-state emitters and the second plurality of solid-state emitters such that: in a third emissions mode, the first plurality of solid-state emitters and the second plurality of solid-state emitters emit light sequentially at a frequency of about 2,000 Hz or greater, producing a combined light output having a third CCT that differs from the first CCT and the second CCT; and provide for changing between the first emissions mode, the second emissions mode, and the third emissions mode based on hysteresis of the lighting switch. In some such instances, in the third emissions mode: the light emitted by the first plurality of solid-state emitters constitutes about 50-75% of the combined light output; the light emitted by the second plurality of solid-state emitters constitutes about 25-50% of the combined light output; and the third CCT is in the range of about 2,500-5,000 K. In some further such instances, in providing for changing between the first emissions mode, the second emissions mode, and the third emissions mode based on hysteresis of the lighting switch, the controller is configured such that: in turning on the solid-state luminaire by toggling the lighting switch from an off position to an on position, the solid-state luminaire enters the first emissions mode; in turning off the solid-state luminaire by toggling the lighting switch from the on position to the off position and then turning on the solid-state luminaire again by toggling the lighting switch from the off position to the on position within a first time window of about 3 seconds or less, the solid-state luminaire transitions from the first emissions mode to the second emissions mode; and in turning off the solid-state luminaire again by toggling the lighting switch from the on position to the off position and then turning on the solid-state luminaire again by toggling the lighting switch from the off position to the on position within a second time window of about 3 seconds or less, the solid-state luminaire transitions from the second emissions mode to the third emissions mode. In some such cases, the first time window and the second time window differ. In some instances, the solid-state luminaire further includes a communication module configured to communicate with the controller, wherein the controller is configured to output the control signal based, at least in part, on input received through the communication module from a source remote to the solid-state luminaire. In some cases, the control signal is a pulse-width modulation (PWM) signal.

Another example embodiment provides a solid-state luminaire including: a light source module including: a first plurality of solid-state emitters configured to emit light having a first correlated color temperature (CCT) in the range of about 1,800-2,300 K; and a second plurality of solid-state emitters configured to emit light having a second CCT in the range of about 5,000-8,000 K. The solid-state luminaire further includes a driver configured to: drive the first plurality of solid-state emitters and the second plurality of solid-state emitters such that: in a first emissions mode, the first plurality of solid-state emitters emits light, wherein a spectral power ratio of the light emitted at a wavelength in the range of about 400-495 nm to a remainder of the light emitted by the first plurality of solid-state emitters in the first emissions mode is such that the light emitted at the wavelength in the range of about 400-495 nm constitutes about 10% or less of a total light emitted by the first plurality of solid-state emitters; and in a second emissions mode, the second plurality of solid-state emitters emits light, wherein a spectral power ratio of the light emitted at a wavelength in the range of about 400-495 nm to a remainder of the light emitted by the second plurality of solid-state emitters in the second emissions mode is such that the light emitted at the wavelength in the range of about 400-495 nm constitutes about 30% or more of a total light emitted by the second plurality of solid-state emitters; and provide for changing between the first emissions mode and the second emissions mode based on hysteresis of a lighting switch associated with the solid-state luminaire. In some cases, in providing for changing between the first emissions mode and the second emissions mode based on hysteresis of the lighting switch, the driver is configured such that: in turning on the solid-state luminaire by toggling the lighting switch from an off position to an on position, the solid-state luminaire enters the first emissions mode; and in turning off the solid-state luminaire by toggling the lighting switch from the on position to the off position and then turning on the solid-state luminaire again by toggling the lighting switch from the off position to the on position within a time window, the solid-state luminaire transitions from the first emissions mode to the second emissions mode. In some cases, the driver is further configured to: drive the first plurality of solid-state emitters and the second plurality of solid-state emitters such that: in a third emissions mode, the first plurality of solid-state emitters and the second plurality of solid-state emitters emit light sequentially at a frequency of about 2,000 Hz or greater, producing a combined light output having a CCT in the range of about 2,500-5,000 K; and provide for changing between the first emissions mode, the second emissions mode, and the third emissions mode based on hysteresis of the lighting switch. In some such cases, in the third emissions mode: the light emitted by the first plurality of solid-state emitters constitutes about 50%-75% of the combined light output; and the light emitted by the second plurality of solid-state emitters constitutes about 25%-50% of the combined light output. In some instances, in providing for changing between the first emissions mode, the second emissions mode, and the third emissions mode based on hysteresis of the lighting switch, the driver is configured such that: in turning on the solid-state luminaire by toggling the lighting switch from an off position to an on position, the solid-state luminaire enters the first emissions mode; in turning off the solid-state luminaire by toggling the lighting switch from the on position to the off position and then turning on the solid-state luminaire again by toggling the lighting switch from the off position to the on position within a first time window, the solid-state luminaire transitions from the first emissions mode to the second emissions mode; and in turning off the solid-state luminaire again by toggling the lighting switch from the on position to the off position and then turning on the solid-state luminaire again by toggling the lighting switch from the off position to the on position within a second time window, the solid-state luminaire transitions from the second emissions mode to the third emissions mode. In some cases, the power source comprises at least one of an electrical outlet and a battery. In some instances: the first plurality of solid-state emitters includes eight emitters operatively coupled in series; and the second plurality of solid-state emitters includes nine emitters operatively coupled in series. In some cases, a lighting system is provided, the lighting system including: a solid-state luminaire configured as provided herein; and a control interface configured to communicate with the driver, wherein the driver is configured to drive the first plurality of solid-state emitters and the second plurality of solid-state emitters based, at least in part, on input received from the control interface.

Another example embodiment provides a method of illumination via a solid-state luminaire, the method including: emitting, via a first solid-state emitter of the solid-state luminaire, light having a first correlated color temperature (CCT) in the range of about 1,800-2,300 K, wherein a spectral power ratio of the light emitted at a wavelength between 400-495 nm to a remainder of the light emitted by the first solid-state emitter is such that the light emitted at the wavelength between 400-495 nm constitutes about 10% or less of a total light emitted by the first solid-state emitter; and emitting, via a second solid-state emitter of the solid-state luminaire, light having a second CCT in the range of about 5,000-8,000 K, wherein a spectral power ratio of the light emitted at a wavelength between 400-495 nm to a remainder of the light emitted by the second solid-state emitter is such that the light emitted at the wavelength between 400-495 nm constitutes about 30% or more of a total light emitted by the second solid-state emitter. In some instances, the method further includes: sequentially performing the emitting via the first solid-state emitter and the emitting via the second solid-state emitter at a frequency of about 2,000 Hz or greater, resulting in a combined light output having a CCT in the range of about 2,500-5,000 K, wherein: the light emitted by the first solid-state emitter constitutes about 50-75% of the combined light output; and the light emitted by the second solid-state emitter constitutes about 25-50% of the combined light output.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future-filed applications claiming priority to this application may claim the disclosed subject matter in a different manner and generally may include any set of one or more limitations as variously disclosed or otherwise demonstrated herein.

What is claimed is:

1. A solid-state luminaire comprising:
   a printed circuit board (PCB);
   a first plurality of solid-state emitters populated over the PCB and configured to emit light having a first correlated color temperature (CCT);
   a second plurality of solid-state emitters populated over the PCB and configured to emit light having a second CCT that differs from the first CCT; and
   a controller configured to:
      electronically control, via a control signal, emissions of the first plurality of solid-state emitters and the second plurality of solid-state emitters such that:
         in a first emissions mode, the first plurality of solid-state emitters emits light, wherein a spectral power ratio of the light emitted at a wavelength in the range of about 400-495 nm to a remainder of the light emitted by the first plurality of solid-state emitters in the first emissions mode is such that the light emitted at the wavelength in the range of about 400-495 nm constitutes about 10% or less of a total light emitted by the first plurality of solid-state emitters; and
         in a second emissions mode, the second plurality of solid-state emitters emits light, wherein a spectral power ratio of the light emitted at a wavelength in the range of about 400-495 nm to a remainder of the light emitted by the second plurality of solid-state emitters in the second emissions mode is such that the light emitted at the wavelength in the range of about 400-495 nm constitutes about 30% or more of a total light emitted by the second plurality of solid-state emitters; and
      provide for changing between the first emissions mode and the second emissions mode based on hysteresis of a lighting switch associated with the solid-state luminaire.

2. The solid-state luminaire of claim 1, wherein:
   the first CCT is in the range of about 1,800-2,300 K; and
   the spectral power ratio of the light emitted at a wavelength in the range of about 400-495 nm to the remainder of the light emitted by the first plurality of solid-state emitters in the first emissions mode is such that the light emitted at the wavelength in the range of about 400-495 nm constitutes about 5% or less of the total light emitted by the first plurality of solid-state emitters.

3. The solid-state luminaire of claim 1, wherein:
   the second CCT is in the range of about 5,000-8,000 K; and
   the spectral power ratio of the light emitted at a wavelength in the range of about 400-495 nm to the remainder of the light emitted by the second plurality of solid-state emitters in the second emissions mode is such that the light emitted at the wavelength in the range of about 400-495 nm constitutes about 40% or more of the total light emitted by the second plurality of solid-state emitters.

4. The solid-state luminaire of claim 1, wherein in providing for changing between the first emissions mode and the second emissions mode based on hysteresis of the lighting switch, the controller is configured such that:
   in turning on the solid-state luminaire by toggling the lighting switch from an off position to an on position, the solid-state luminaire enters the first emissions mode; and
   in turning off the solid-state luminaire by toggling the lighting switch from the on position to the off position and then turning on the solid-state luminaire again by toggling the lighting switch from the off position to the on position within a time window of about 3 seconds or less, the solid-state luminaire transitions from the first emissions mode to the second emissions mode.

5. The solid-state luminaire of claim 1, wherein the controller is further configured to:
   electronically control, via the control signal, emissions of both the first plurality of solid-state emitters and the second plurality of solid-state emitters such that:
      in a third emissions mode, the first plurality of solid-state emitters and the second plurality of solid-state emitters emit light sequentially at a frequency of about 2,000 Hz or greater, producing a combined light output having a third CCT that differs from the first CCT and the second CCT; and
   provide for changing between the first emissions mode, the second emissions mode, and the third emissions mode based on hysteresis of the lighting switch.

6. The solid-state luminaire of claim 5, wherein in the third emissions mode:
   the light emitted by the first plurality of solid-state emitters constitutes about 50-75% of the combined light output;
   the light emitted by the second plurality of solid-state emitters constitutes about 25-50% of the combined light output; and
   the third CCT is in the range of about 2,500-5,000 K.

7. The solid-state luminaire of claim 5, wherein in providing for changing between the first emissions mode, the second emissions mode, and the third emissions mode based on hysteresis of the lighting switch, the controller is configured such that:
   in turning on the solid-state luminaire by toggling the lighting switch from an off position to an on position, the solid-state luminaire enters the first emissions mode;
   in turning off the solid-state luminaire by toggling the lighting switch from the on position to the off position and then turning on the solid-state luminaire again by toggling the lighting switch from the off position to the on position within a first time window of about 3 seconds or less, the solid-state luminaire transitions from the first emissions mode to the second emissions mode; and
   in turning off the solid-state luminaire again by toggling the lighting switch from the on position to the off position and then turning on the solid-state luminaire again by toggling the lighting switch from the off position to the on position within a second time window of about 3 seconds or less, the solid-state luminaire transitions from the second emissions mode to the third emissions mode.

8. The solid-state luminaire of claim 7, wherein the first time window and the second time window differ.

9. The solid-state luminaire of claim 1, further comprising a communication module configured to communicate with the controller, wherein the controller is configured to output the control signal based, at least in part, on input received through the communication module from a source remote to the solid-state luminaire.

10. The solid-state luminaire of claim 1, wherein the control signal is a pulse-width modulation (PWM) signal.

11. A solid-state luminaire comprising:
a light source module comprising:
a first plurality of solid-state emitters configured to emit light having a first correlated color temperature (CCT) in the range of about 1,800-2,300 K; and
a second plurality of solid-state emitters configured to emit light having a second CCT in the range of about 5,000-8,000 K; and
a driver configured to:
drive the first plurality of solid-state emitters and the second plurality of solid-state emitters such that:
in a first emissions mode, the first plurality of solid-state emitters emits light, wherein a spectral power ratio of the light emitted at a wavelength in the range of about 400-495 nm to a remainder of the light emitted by the first plurality of solid-state emitters in the first emissions mode is such that the light emitted at the wavelength in the range of about 400-495 nm constitutes about 10% or less of a total light emitted by the first plurality of solid-state emitters; and
in a second emissions mode, the second plurality of solid-state emitters emits light, wherein a spectral power ratio of the light emitted at a wavelength in the range of about 400-495 nm to a remainder of the light emitted by the second plurality of solid-state emitters in the second emissions mode is such that the light emitted at the wavelength in the range of about 400-495 nm constitutes about 30% or more of a total light emitted by the second plurality of solid-state emitters; and
provide for changing between the first emissions mode and the second emissions mode based on hysteresis of a lighting switch associated with the solid-state luminaire.

12. The solid-state luminaire of claim 11, wherein in providing for changing between the first emissions mode and the second emissions mode based on hysteresis of the lighting switch, the driver is configured such that:
in turning on the solid-state luminaire by toggling the lighting switch from an off position to an on position, the solid-state luminaire enters the first emissions mode; and
in turning off the solid-state luminaire by toggling the lighting switch from the on position to the off position and then turning on the solid-state luminaire again by toggling the lighting switch from the off position to the on position within a time window, the solid-state luminaire transitions from the first emissions mode to the second emissions mode.

13. The solid-state luminaire of claim 11, wherein the driver is further configured to:
drive the first plurality of solid-state emitters and the second plurality of solid-state emitters such that:
in a third emissions mode, the first plurality of solid-state emitters and the second plurality of solid-state emitters emit light sequentially at a frequency of about 2,000 Hz or greater, producing a combined light output having a CCT in the range of about 2,500-5,000 K; and
provide for changing between the first emissions mode, the second emissions mode, and the third emissions mode based on hysteresis of the lighting switch.

14. The solid-state luminaire of claim 13, wherein in the third emissions mode:
the light emitted by the first plurality of solid-state emitters constitutes about 50%-75% of the combined light output; and
the light emitted by the second plurality of solid-state emitters constitutes about 25%-50% of the combined light output.

15. The solid-state luminaire of claim 13, wherein in providing for changing between the first emissions mode, the second emissions mode, and the third emissions mode based on hysteresis of the lighting switch, the driver is configured such that:
in turning on the solid-state luminaire by toggling the lighting switch from an off position to an on position, the solid-state luminaire enters the first emissions mode;
in turning off the solid-state luminaire by toggling the lighting switch from the on position to the off position and then turning on the solid-state luminaire again by toggling the lighting switch from the off position to the on position within a first time window, the solid-state luminaire transitions from the first emissions mode to the second emissions mode; and
in turning off the solid-state luminaire again by toggling the lighting switch from the on position to the off position and then turning on the solid-state luminaire again by toggling the lighting switch from the off position to the on position within a second time window, the solid-state luminaire transitions from the second emissions mode to the third emissions mode.

16. The solid-state luminaire of claim 11, wherein the power source comprises at least one of an electrical outlet and a battery.

17. The solid-state luminaire of claim 11, wherein:
the first plurality of solid-state emitters includes eight emitters operatively coupled in series; and
the second plurality of solid-state emitters includes nine emitters operatively coupled in series.

18. A lighting system comprising:
the solid-state luminaire of claim 11; and
a control interface configured to communicate with the driver, wherein the driver is configured to drive the first plurality of solid-state emitters and the second plurality of solid-state emitters based, at least in part, on input received from the control interface.

19. A method of illumination via a solid-state luminaire, the method comprising:
emitting, via a first solid-state emitter of the solid-state luminaire, light having a first correlated color temperature (CCT) in the range of about 1,800-2,300 K, wherein a spectral power ratio of the light emitted at a wavelength between 400-495 nm to a remainder of the light emitted by the first solid-state emitter is such that the light emitted at the wavelength between 400-495 nm constitutes about 10% or less of a total light emitted by the first solid-state emitter; and
emitting, via a second solid-state emitter of the solid-state luminaire, light having a second CCT in the range of about 5,000-8,000 K, wherein a spectral power ratio of the light emitted at a wavelength between 400-495 nm to a remainder of the light emitted by the second solid-state emitter is such that the light emitted at the wavelength between 400-495 nm constitutes about 30% or more of a total light emitted by the second solid-state emitter.

20. The method of claim 19, further comprising:
sequentially performing the emitting via the first solid-state emitter and the emitting via the second solid-state emitter at a frequency of about 2,000 Hz or greater, resulting in a combined light output having a CCT in the range of about 2,500-5,000 K,
wherein:
the light emitted by the first solid-state emitter constitutes about 50-75% of the combined light output; and
the light emitted by the second solid-state emitter constitutes about 25-50% of the combined light output.

* * * * *